United States Patent
Gross et al.

(10) Patent No.: US 9,012,194 B2
(45) Date of Patent: Apr. 21, 2015

(54) SOPHOROLIPIDS AS PROTEIN INDUCERS AND INHIBITORS IN FERMENTATION MEDIUM

(75) Inventors: Richard A. Gross, Plainview, NY (US); Vishal Shah, Plainsboro, NJ (US); Frantisek Nerud, Prague (CZ); Datta Madamwars, Vallabh Vidyanagar (IN)

(73) Assignee: Synthezyme LLC, Troy, NY (US)

( * ) Notice: Subject to any disclaimer, the term of this patent is extended or adjusted under 35 U.S.C. 154(b) by 1383 days.

(21) Appl. No.: 11/722,356

(22) PCT Filed: Dec. 22, 2005

(86) PCT No.: PCT/US2005/046457
§ 371 (c)(1),
(2), (4) Date: Dec. 11, 2007

(87) PCT Pub. No.: WO2007/073371
PCT Pub. Date: Jun. 28, 2007

(65) Prior Publication Data
US 2008/0076165 A1    Mar. 27, 2008

Related U.S. Application Data

(60) Provisional application No. 60/638,747, filed on Dec. 22, 2004.

(51) Int. Cl.
C12P 21/00 (2006.01)
C12P 19/44 (2006.01)
C12P 19/62 (2006.01)

(52) U.S. Cl.
CPC ............... C12P 21/00 (2013.01); C12P 19/44 (2013.01); C12P 19/62 (2013.01)

(58) Field of Classification Search
None
See application file for complete search history.

(56) References Cited

PUBLICATIONS

Daniel H-J et al. Production of sophorolipids in high concentration from deproteinized whey and rapeseed oil in a two stage fed batch process using *Candida bombicola* ATCC 22214 and *Cryptococcus curvatus* ATCC 20509, Biotechnology Letters, Dec. 1998, vol. 20, No. 12, pp. 1153-1156.*
Faith W.T. et al. Production and applications of enzymes, Advances in Biochemical Engineering/Biotechnology, 1971, vol. 1. pp. 77-111.*
Ramos C. et al. Effect of Tributylphenyltetraethoxylate on Enzyme Production of *Pleurotus ostreatus*, Applied Biochemistry and Biotechnology, 2003, vol. 110, pp. 33-44.*
Hrmova M. et al. Induction of cellulose- and xylan-degrading enzyme systems in *Aspergillus terreus* by homo- and heterodisaccharides composed of glucose and xylose, Journal of Genereal Microbiology, 1991, vol. 137, pp. 541-547.*
Helle S.S. et al, Effect of Surfactants on Cellulose Hydrolysis, Biotechnology and Bioengineering, 1993, vol. 42, pp. 611-617.*
Shah V. et al., Influence of dimethyl sulfoxide on extracellular enzyme production by *Pleurotus ostreatus*, Biotechnology Letters, 2006, vol. 28, pp. 651-655.*
Eichlerova I. et al., Ability of industrial dyes decolorization and ligninolytic enzymes production by different *Pleurotus* species with special attention on *Pleurotus calyptratus*, strain CCBAS 461, Process Biochemistry, 2006, vol. 41, pp. 941-946.*
International Preliminary Report on Patentability/Written Opinion, Jun. 24, 2008, The International Bureau of WIPO, Geneva, Switzerland.

* cited by examiner

*Primary Examiner* — Satyendra Singh
(74) *Attorney, Agent, or Firm* — Laurence P. Colton; Smith Risley Tempel Santos LLC

(57) ABSTRACT

A method for producing sophorolipids having protein inducer and/or repressor activities having the steps of synthesizing the sophorolipid by fermentation of *Candida bombicola* in a fermentation media to form a natural mixture of lactonic sophorolipids and non-lactonic sophorolipids and then utilizing the natural mixture as a protein inducing agent, utilizing the natural mixture as a protein repressing agent, and/or utilizing the natural mixture as a combined protein induction/repressor agent. An application of the sophorolipid compound produced according to the method as a microbial media component.

5 Claims, 1 Drawing Sheet

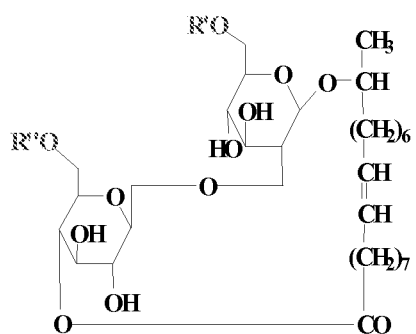 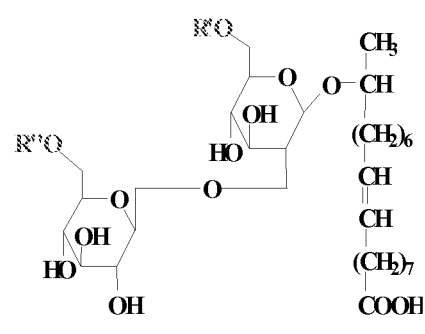
a. Lactonic sophorolipid        b. Open ring sophorolipid
**Structures of sophorolipids produced by *Candida bombicola***

SOPHOROLIPIDS AS PROTEIN INDUCERS AND INHIBITORS IN FERMENTATION MEDIUM

STATEMENT OF RELATED APPLICATIONS

This patent application is the Patent Cooperation Treaty (PCT) Chapter II National Phase application in the United States of America of International Application No. PCT/US2005/046457 having an International Filing Date of 22 Dec. 2005, which is based on and claims priority on U.S. Provisional Patent Application No. 60/638,747 having a filing date of 22 Dec. 2004.

BACKGROUND OF THE INVENTION

1. Technical Field

The present invention in general relates to the field of uses for sophorolipids and more specifically to the field of protein inducers and as a media component. The invention is directed to developing low cost inducers/repressors for protein production.

2. Prior Art

For production of proteins on a larger scale, a need exists for cheap and well defined molecules to act as inducers of the protein of interest and also as a repressor for unwanted enzymes. This aids in higher yields, decreasing the purification costs and enhancing the profits. Sophorose has been shown to be a good inducer of cellulase protein. See Hrmova, M., Petrakova, E., Biely, P., Journal of General Microbiology 137, 541-547 (1991). However, the cost of the molecule makes it impractical to be used at commercial level.

Sophorolipids are microbial extracellular glycolipids produced by resting cells of *Candida bombicola*. The chemical composition of sophorolipid is constituted by a disaccharide sugar viz. sophorose and a fatty acid or an ester group. *Candida bombicola* produces the sophorolipids as a mixture of macroloctones and free acid structures that are acetylated to various extents at the primary hydroxyl sophorose ring positions (FIG. 1). See Bisht, K. S. et al., J. Org. Chem., vol. 64, pp. 780-789 (1999).

It is to the development of sophorolipids for production and industrial purposes, and other purposes, that the present invention is directed.

BRIEF SUMMARY OF THE INVENTION

A natural mixture of sophorolipids was synthesized by fermentation of *Candida bombicola*. When *B. subtilis* was grown in presence of sophorolipids, increased production of amylase was observed. When *Pleurotus ostreatus* 473 strain, which produces both laccase and manganese peroxidase, was grown in the presence of sophorolipids, increased production of laccase was observed while the production of manganese peroxidase decreased.

Thus, the applications of sophorolipids in the fields of industry and basic sciences would have tremendous advantages in higher production or inhibition rates of proteins. Further, while sophorolipids can find applications in diversified fields, the present invention indicates that sophorolipids could be used as protein inducers and repressors.

These features, and other features and advantages of the present invention, will become more apparent to those of ordinary skill in the relevant art when the following detailed description of the preferred embodiments is read in conjunction with the appended drawing.

BRIEF DESCRIPTION OF THE FIGURE

FIG. 1 are representative structures of sophorolipids produced by *Candida bombicola*, with FIG. 1a showing lactonic sophorolipid and FIG. 1b showing open ring sophorolipid.

DETAILED DESCRIPTION OF THE PREFERRED EMBODIMENTS

1. Sophorolipid Fermentation

Sophorolipids were synthesized by fermentation of *Candida bombicola*. The fermentation media was composed of glucose 100 g, yeast extract 10 g, urea 1 g and oleic acid 40 g in 1000 ml of water. After 7 days of fermentation, sophorolipid was extracted thrice using ethyl acetate. The extracts were pooled and the solvent then was removed. The obtained product was therein washed with hexane to remove the residual fatty acids. This was "natural" sophorolipid. The sophorolipid was dried in a vacuum desiccator.

2. Study of Amylase Protein Induction

*Bacillus subtilis* strain was used to study the effect of sophorolipid on amylase induction. Culture was grown on Peptone: 5 gm/L, Beef extract: 3 gm/L and Starch: 2 gm/L. A single colony of *Bacillus subtilis* was inoculated in 10 ml medium and was allowed to grow for 12 hours. After the culture reached to the log phase, 1 ml of the same was inoculated in 100 ml of the medium. Control experiments having no sophorolipids also were conducted, whereas the experimental set has 1 mM of sophorolipid prepared in DMSO.

After 48 hours a sample was withdrawn, centrifuged at 8000 rpm for 20 minutes, and amylase activity determined using standard methods.

3. Study of Laccase Protein Induction and Manganese Peroxidase Repression

*Pleurotus ostreatus* 473 was used to study the effect of sophorolipids on Laccase/Manganese peroxidase production. Culture was cultivated in agar medium containing 5 g/L cellulose, 1 g/L $KH_2PO_4$, 0.5 g/L $MgSO_4.7H_2O$, 0.2 g/L ammonium tartrate, 0.2 g/L $NaH_2PO_4$, 50 mg/L $CaCl_2$, 50 mg/L, $FeSO_4.7H_2O$, 10 mg/L $CuSO_4.5H_2O$, 5 mg/L $ZnSO_4.7H_2O$, 5 mg/L $MnSO_4.4H_2O$ and 25 g/L agar. pH of the medium was 6.0. For enzyme production studies, flasks with 20 mL of the above media (without agar) were inoculated with two wort agar plugs (2° Balling, 10 mm diameter), cut from the actively growing part of a colony on a Petri dish, and incubated at 27° C. for 14 days. After 14 days a sample was withdrawn, centrifuged at 8000 rpm for 20 minutes and laccase and MnP activity determined using standard methods.

RESULTS AND DISCUSSION

As shown in Table 1, upon growing *B. subtilis* in the presence of sophorolipid, an increase of 39% amylase protein production observed. Growing *Pleurotus ostreatus* 473 in the presence of 1 mM sophorolipid natural mixture resulted in 4.5 times increase in laccase protein whereas there was a decrease of 25% in the production of manganese peroxidase protein. This shows that the sophorolipid natural mixture has the ability to act as an inducer for some proteins and the ability to act as a repressor for others.

The invention will find its place in industries that produce protein products such as enzymes through microbial fermentation. Also, microbial media that has sophorolipids as a component can be sold for protein induction studies.

Sophorolipids will be administered in the fermentation medium as either fine powder or in the form of solutions prepared in DMSO, alkaline sucrose solution, chloroform, methanol or ethyl acetate.

TABLE 1

% Increase/decrease of enzyme production

| Enzyme | % values |
|---|---|
| Laccase | |
| Control | 100 |
| Sophorolipid Induced | 453 |
| Manganese peroxidase | |
| Control | 100 |
| Sophorolipid Induced | 73 |
| Amylase | |
| Control | 100 |
| Sophorolipid induced | 139 |

The foregoing detailed descriptions of the preferred embodiments and the appended FIGURE have been presented only for illustrative and descriptive purposes and are not intended to be exhaustive or to limit the scope and spirit of the invention. The embodiments were selected and described to best explain the principles of the invention and its practical applications. One skilled in the art will recognize that many variations can be made to the invention disclosed in this specification without departing from the scope and spirit of the invention

What is claimed is:

1. A method for inducing the production of a protein, comprising:
    a) synthesizing sophorolipids by fermentation of *Candida bombicola* in a fermentation medium;
    b) after 7 days of fermentation, extracting the sophorolipids produced from the fermentation medium;
    c) washing the extracted sophorolipids to remove residual fatty acids to form a natural mixture of lactonic sophorolipids and non-lactonic sophorolipids; and
    d) adding an effective amount of the natural mixture of lactonic sophorolipids and non-lactonic sophorolipids as protein inducing agent to a microbial culture medium during protein production by *Bacillus subtilis* cells in said culture medium,
    wherein the protein is amylase, and
    whereby the production of the amylase protein is significantly increased.

2. A method for inducing the production of amylase protein, comprising:
    a) synthesizing sophorolipids by fermentation of *Candida bombicola* in a fermentation medium;
    b) after 7 days of fermentation, extracting the sophorolipids thrice using ethyl acetate as a solvent;
    c) pooling the extracted sophorolipids and removing the solvent;
    d) washing the extracted sophorolipids with hexane to remove residual fatty acids to form a natural mixture of lactonic sophorolipids and non-lactonic sophorolipids; and
    e) adding an effective amount of the natural mixture of lactonic sophorolipids and non-lactonic sophorolipids as protein inducing agent to a microbial culture medium during protein production by *Bacillus subtilis* cells in said culture medium,
    wherein said fermentation medium comprises 100 g of glucose, 10 g of yeast extract, 1 g of urea, and 40 g of oleic acid in 1000 ml of water, and whereby the production of the amylase protein is significantly increased.

3. The method as claimed in claim 2, further comprising:
    a) growing the *Bacillus subtilis* cells in the culture medium comprising 5 gm/L peptone, 3 gm/L beef extract, and 2 gm/L starch;
    b) inoculating the *Bacillus subtilis* cells in 10 ml of the culture medium and allowing the *Bacillus subtilis* cells to grow for 12 hours; and
    c) after the *Bacillus subtilis* reaches the log phase, inoculating 1 ml of the log phase *Bacillus subtilis* cells in 100 ml of the culture medium.

4. The method as claimed in claim 3, further comprising adding the natural mixture of sophorolipids to the culture medium as a fine powder.

5. The method as claimed in claim 3, further comprising adding the natural mixture of sophorolipids to the culture medium in the form of a solution prepared in DMSO, alkaline sucrose solution, chloroform, methanol, or ethyl acetate.

* * * * *